United States Patent
Bear et al.

(10) Patent No.: US 8,985,359 B2
(45) Date of Patent: Mar. 24, 2015

(54) CONTAINER CAP WITH KINK-RESISTANT CONNECTOR

(75) Inventors: Adam J Bear, Gorham, ME (US); Gail H Pentheny, Dover, NH (US); Paul Kevin Seeto, Clinton, MA (US)

(73) Assignee: Corning Incorporated, Corning, NY (US)

( * ) Notice: Subject to any disclaimer, the term of this patent is extended or adjusted under 35 U.S.C. 154(b) by 130 days.

(21) Appl. No.: 13/429,961

(22) Filed: Mar. 26, 2012

(65) Prior Publication Data

US 2012/0248111 A1 Oct. 4, 2012

Related U.S. Application Data

(60) Provisional application No. 61/468,295, filed on Mar. 28, 2011.

(51) Int. Cl.
*C12M 3/04* (2006.01)
*B01L 3/00* (2006.01)
*B65D 47/06* (2006.01)
*A61J 1/14* (2006.01)
*C12M 1/00* (2006.01)

(52) U.S. Cl.
CPC ............. *B01L 3/50825* (2013.01); *B65D 47/06* (2013.01); *A61J 1/1475* (2013.01); *C12M 23/38* (2013.01); *C12M 27/12* (2013.01)
USPC .......................................... 215/309

(58) Field of Classification Search
CPC ...... C12M 27/12; C12M 23/38; C12M 27/10; B01L 3/50825; B65D 47/06; A61J 1/1475
USPC .......... 215/247–249, 277, 309; 604/403, 408, 604/411, 415; 435/298.2; 285/124.4, 136.1; 366/213; 494/41
See application file for complete search history.

(56) References Cited

U.S. PATENT DOCUMENTS

| | | | | |
|---|---|---|---|---|
| 2,276,421 A | * | 3/1942 | Ross | 215/247 |
| 3,217,982 A | * | 11/1965 | Wilsmann et al. | 494/41 |
| 3,512,806 A | * | 5/1970 | Fullmer et al. | 285/124.4 |
| 3,540,700 A | | 11/1970 | Freedman et al. | 259/3 |
| 3,685,680 A | * | 8/1972 | Tenckhoff et al. | 220/277 |
| 3,740,321 A | | 6/1973 | Pagano et al. | |
| 3,779,585 A | * | 12/1973 | Handzlik | 285/136.1 |
| 3,823,840 A | * | 7/1974 | Zackheim | 215/247 |
| 4,209,176 A | * | 6/1980 | Soodak et al. | 277/397 |
| 4,289,854 A | | 9/1981 | Tolbert et al. | |
| 4,330,216 A | | 5/1982 | Johnson | |

(Continued)

FOREIGN PATENT DOCUMENTS

| | | |
|---|---|---|
| EP | 0657382 | 6/1995 |
| EP | 1400283 | 3/2004 |

(Continued)

*Primary Examiner* — Fenn Mathew
*Assistant Examiner* — James N Smalley
(74) *Attorney, Agent, or Firm* — Michael W Russell

(57) ABSTRACT

A cap for use in a neck of a laboratory vessel, such as a roller bottle, is disclosed. In embodiments, the cap is assembled from two parts, an annular skirted cap body and a cap insert. In embodiments the cap insert has integral connectors for attaching tubing, vents, filters, or the like. In embodiments, the cap insert fits into the annular skirted cap body through a rotatable fitting. In embodiments, when the cap is assembled, the top portion of the cap, having integral connectors, is rotatably fitted to the annular side wall of the cap.

19 Claims, 8 Drawing Sheets

(56) References Cited

U.S. PATENT DOCUMENTS

| | | | |
|---|---|---|---|
| 4,747,500 A | 5/1988 | Gach et al. | |
| 4,920,766 A * | 5/1990 | Yamamoto et al. | 62/474 |
| 5,188,628 A * | 2/1993 | Rani et al. | 604/405 |
| 5,514,070 A * | 5/1996 | Pages | 494/41 |
| 5,848,622 A * | 12/1998 | Kilcoin | 141/59 |
| 6,066,497 A | 5/2000 | Powell | 435/298.2 |
| 6,150,159 A | 11/2000 | Fry | 435/304.1 |
| 7,163,115 B2 | 1/2007 | Whitley | 215/276 |
| 2004/0156650 A1 | 8/2004 | Ziegelmuller et al. | 399/102 |
| 2005/0029258 A1 | 2/2005 | Juliano et al. | 220/4.23 |
| 2007/0257447 A1 | 11/2007 | Petrak | 277/551 |
| 2009/0148941 A1 | 6/2009 | Florez et al. | 435/325 |
| 2010/0147846 A1 | 6/2010 | Soibel et al. | 220/202 |

FOREIGN PATENT DOCUMENTS

| | | |
|---|---|---|
| GB | 2235741 | 3/1991 |
| GB | 2244532 | 4/1991 |
| JP | 224505 | 8/2002 |
| JP | 154219 | 5/2003 |
| JP | 59707 | 3/2005 |
| JP | 81911 | 3/2005 |
| JP | 182250 | 7/2006 |
| JP | 4601137 | 10/2012 |
| WO | WO02072265 | 9/2000 |

* cited by examiner

CONTAINER CAP WITH KINK-RESISTANT CONNECTOR

CROSS-REFERENCE TO RELATED APPLICATIONS

This application claims the benefit of priority under 35 U.S.C. §119 of U.S. Provisional Application Ser. No. 61/468,295 filed on Mar. 28, 2011, the content of which is relied upon and incorporated herein by reference in its entirety.

FIELD

This disclosure pertains to improved laboratory apparatus. More specifically, the disclosure relates to caps for use with rotating laboratory apparatus. In embodiments, the caps have connectors and a rotating mechanism to prevent twisting or kinking of equipment connected to the caps.

BACKGROUND

Roller bottles are used in many laboratory and other applications. In general, roller bottles are cylindrical containers structured and arranged to rotate around a long axis when placed on a roller apparatus. This rolling motion increases the surface area available to cells for culture, and continually mixes cells and media in culture. Roller bottles may be used in cell and tissue culture applications for aseptic sampling, tissue and cell culture in media, pilot and process research and development, and sterile filling and transfer of liquid components of tissue and cell culture. In these applications, it is important to work with an aseptic closed system. The aseptic closed system often includes a vessel to hold the cell culture media with direct access to the media by way of a tubing accessory set that passes through the vessel cap. The tubing accessory set can include, for example, dip tubes, tubing, filters, Y connectors and quick connectors. Venting with tubing, which may require filtering may also be needed. Media can be placed or displaced within the vessel by way of pressure such as a vacuum pump, gravity or even a syringe. Each time that a tissue or cell culture container is manipulated manually, for example to remove or replace a lid, screw a lid onto a container or to insert a tube into a container, there is an increased risk of contamination of the culture. Therefore, there is a need for a roller bottle closure apparatus that both supports the maintenance of an aseptic environment and also allows for the motion of a roller bottle while still allowing the bottle to remain connected to accessories such as tubing passing through the vessel cap.

SUMMARY

In embodiments, an additional bearing is used. In embodiments, a thrust bearing sits on a top surface of the annular skirted cap body. Secured to the top surface of the thrust bearing is an annular anti-rotation mounting plate. The cap insert, with at least one protruding port, is secured to the annular anti-rotation mounting plate. When two bearings are utilized, the annular skirted cap body, secured to a container, rotates with the container.

In an embodiment (1) a cap apparatus is disclosed having a cap apparatus assembled from two parts; (1) an annular skirted cap body having a side wall and a central opening defining an outer surface of the cap body, an annular top wall having an annular outer surface and an annular undersurface, a flanged bearing secured to an undersurface of the annular top wall, and an annular thrust bearing secured to the annular outer surface of the annular skirted side body, the thrust bearing having an outer surface; and, (2) a cap insert having at least one port; wherein the inner surface of the annular skirted cap body has a connector to connect the skirted side body to a container; wherein the cap insert is seated inside the skirted cap body so that the annular skirted cap body and the cap inserted are coupled through the flanged bearing, and the at least one port extends through the central opening of the annular skirted cap body; and wherein the top face of the cap insert is attached to an annular anti-rotation mounting plate. In an aspect (2) the cap apparatus of aspect 1 is described, further comprising an O-ring seated against the flanged bearing. In an aspect (3) the cap apparatus of aspect 2 is described wherein the O-ring is seated between the flanged bearing and the cap insert. In an aspect (4), the cap apparatus of any one of aspects 1-3 are described aspect 1 is described wherein the cap insert has at least two ports. In an aspect (5) the cap apparatus of any one of aspects 1-4 are described wherein the cap insert comprises a vent. In an aspect (6) the cap apparatus of any one of aspects 1-5 are described wherein the cap insert comprises a filter. In an aspect (7) the cap apparatus of aspect5 is described wherein the vent comprises an adjustable vent opening. In an aspect (8) the apparatus of aspect 1 is disclosed further comprising a container structured and arranged to engage with the cap apparatus. In an aspect (9), the cap apparatus of aspect 8 is described wherein the container comprises threading. In an aspect (10), the cap apparatus of aspect 9 is described wherein the cap comprises threading structured and arranged to engage with the threading of the container, to secure the cap against a container. In an aspect (11), the cap apparatus of aspect 10 is described wherein the cap is removably secured to the container. In an aspect (12), the cap apparatus of aspect 10 is described wherein the cap is permanently secured to the container. In an aspect (13) the cap apparatus of aspect 1 is described wherein annular skirted cap body is double skirted. In an aspect (14), the cap apparatus of aspect 1 is disclosed wherein the annular anti-rotation mounting plate comprises mounting holes. In an aspect (15), the cap apparatus of aspect 14 is disclosed wherein the mounting holes are threaded.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

DETAILED DESCRIPTION

Figure 1:
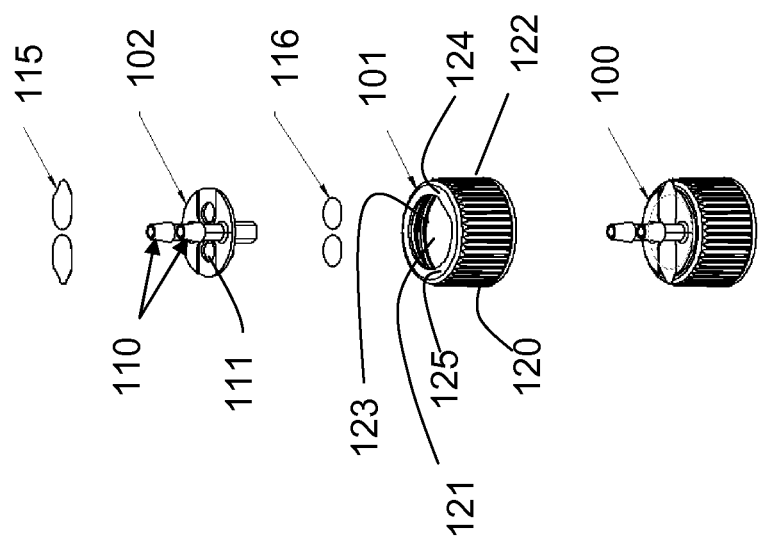
FIG. 1 is an exploded view of an embodiment of a cap apparatus.

A cap apparatus for use in a neck of a container, such as a roller bottle, is disclosed. In embodiments, the cap is assembled from two parts, an annular skirted cap body and a cap insert. Once assembled, the cap is an integral part. In embodiments the cap insert has integral connectors for attaching tubing, vents, filters, or the like. In embodiments, the cap insert fits into the annular skirted cap body and couples to the annular skirted cap body through at least one rotatable fitting. In embodiments, when the cap is assembled, the cap insert of the cap apparatus is rotatably fitted to the annular skirted cap body. That is, the cap apparatus functions to allow the annular skirted cap body of the cap to be secured to a container, while the cap insert portion, having features such as ports or vents, is free to rotate in relation to annular skirted cap body and the container. Thus, when the container (and the annular skirted cap body of the cap apparatus) rotates, the cap insert portion can remain in a relatively stationary orientation, which prevents tubing attached to the ports from twisting or kinking.

In certain applications, such as tissue and cell culture, cell culture containers such as roller bottles are rotated. Rotating cells and tissues in culture may increase the efficiency of cultures, and support healthy cells. Often, during culture, air exchange is provided to the culture through a vented cap. In order to move liquids, including cells and media for example, into and out of roller bottles, caps having connectors are often attached to the bottles. These caps may have ports that are structured and arranged to couple with tubing to allow for the movement of liquids or gasses into or out of culture containers. Often, when it becomes necessary to stop rotating a cell culture container and move liquid into or out of the container, the cap must be changed. To change a cap from a cap having a vent to a cap having a tube connector, an operator must remove the first cap and exchange it for another cap. Each time this occurs, especially when this exchange is performed by a human operator, there is a risk of contaminating the culture. In addition, this type of manipulation of cell culture containers is labor and time intensive. Therefore, there is a need for a cell culture container that does not require changing a cap in order to introduce a tube connector.

Roller bottles are typically filled vertically and then laid horizontally on a roller machine. The vessel is not filled completely. Care is taken when the bottle is placed horizontally so that the vent membrane does not get wet with cell media. The bottle sits on and between two rotating rollers. The rotating rollers may have a rubber compound covering to provide friction to the roller bottle. The rolling action of the roller bottle provides increase exposure of the cells to oxygen for increased cell growth.

It may be preferable to have a connection, for example as a tube connection, to a roller bottle, while the bottle is rolling. If a container is directly connected to tubing, through a cap having a tubing connector for example, and the container is rotated, the tubing would rapidly become entangled. Therefore, there is a need for a container that can be rotated while attached to tubing, without causing the tubing to become entangled.

A cap apparatus for use in a neck of a container, such as a roller bottle, is disclosed. In embodiments, the cap apparatus is assembled from two parts, an annular skirted cap body having a skirted annular side wall and a central opening, and a cap insert. In embodiments, the cap insert has at least one port, and may have additional features such as one or more vents or one or more filter features. The annular skirted cap body may be secured to a container, removably or permanently. In embodiments, the annular skirted cap body has threads or snap-fittings to attach the cap apparatus to a container. In embodiments, a flanged bearing is inserted into the cap body, and then the cap insert is inserted into the cap body. The flanged bearing is seated between the cap insert and the cap body, forming a coupling that allows the two parts, the annular skirted cap body and the cap insert to slidingly rotate in relation to each other. Optionally, an O-ring may be seated beneath the flanged bearing. The O-ring may function to keep debris that might form from friction between the flanged bearing and the annular skirted cap body or the cap insert, from entering the cell culture container.

In embodiments, an additional bearing is used. In embodiments, a thrust bearing sits on a top surface of the annular skirted cap body. Secured to the top surface of the thrust bearing is an annular anti-rotation mounting plate. The cap insert, with at least one protruding port, is secured to the annular anti-rotation mounting plate. When two bearings are utilized, the annular skirted cap body, secured to a container, rotates with the container. In this embodiment, the cap insert is rotatably coupled to the annular skirted cap body in two locations: (1) through a flanged bearing and (2) through the annular anti-rotation mounting plate which is rotatably coupled to the annular skirted cap body through a thrust bearing. The port or ports may be connected to an external stationary port connection. For example, the ports may be connected to tubing that extends from the cap, and holds the cap insert ports, and therefore the cap insert, stationary.

When the cap is secured to a container, and the container is rotated, the annular skirted cap body rotates, because the annular skirted cap body is secured to the container. However, the cap insert, seated against the flanged bearing inside the annular skirted cap body and optionally the annular anti-rotation mounting plate which is secured to a thrust bearing on the top side of the cap body, can remain stationary.

This mechanism allows a rotating container to remain secured to a stationary point, such as tubing, while rotating. When the cap includes both a venting feature and a tube connector feature or port, the container/cap combination may be utilized without requiring a change of caps from a vented cap to a cap with a port. This reduces the number of cap changes and reduces the risk of culture contamination.

Reference will now be made in detail to the present preferred embodiment(s), an example of which is/are illustrated in the accompanying drawings. Whenever possible, the same reference numerals will be used throughout the drawings to refer to the same or like parts.

FIG. 1 is an exploded view of an embodiment of a cap. FIG. 1 shows a cap 100 which is assembled from an annular skirted cap body 101 and a cap insert 102. As shown in FIG. 1, the annular skirted cap body 101 has a side wall 120 and a central opening 121 defining an outer surface 122 of the annular skirted cap body 101, an inner surface 123 of the annular skirted cap body 101 and an annular top wall 124 having an annular outer surface 125 and an annular undersurface (not shown). In the embodiment illustrated in FIG. 1, two ports 110 are shown, along with two vent openings 111. In addition, shown in FIG. 1, the vent openings may be open or closed. In embodiments, the vent openings may be closed using, for example, foil seals 115. In additional embodiments, the vent openings 111 may be opened or closed using a sliding vent closing mechanism (not shown). In embodiments, vent openings 111 may be filled with filter material 116 to prevent material from entering the cell culture container.

Figure 2:
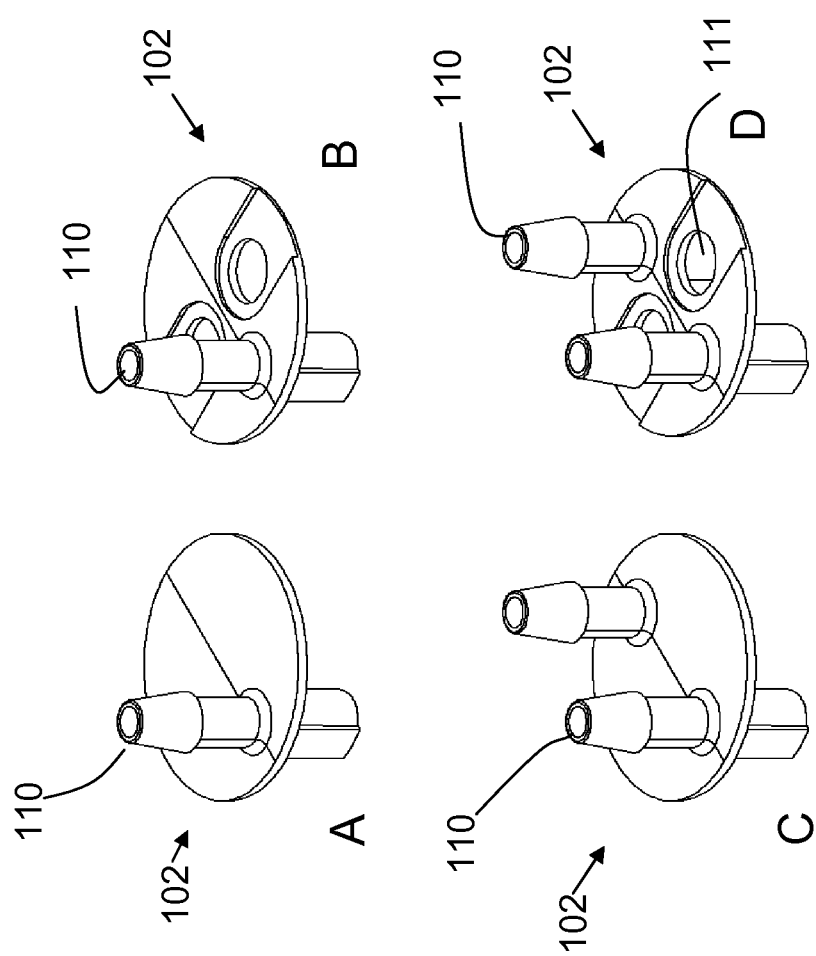
FIG. 2A-D are illustrations of four embodiments (A, B, C and D) of cap inserts.

FIG. 2A-D are illustrations of four embodiments (A, B, C and D) of cap inserts. FIG. 2A shows a cap insert 102 having 1 port 110, and no vents. FIG. 2B shows a cap insert 102 having 1 port 110 and two vents 111. FIG. 2C shows a cap insert 102 having 2 ports 110 and no vents. FIG. 2D shows a cap insert 102 having 2 ports 110 and two vents 111. FIG. 2 illustrates that the cap insert 102 may be available in many configurations, according to the needs of the user. Because of the way that the cap apparatus are assembled, there is considerable flexibility in the cap inserts 102 that may be coupled to a cap body. That is, when manufacturing the cap apparatus, the manufacturer has flexibility in choosing the cap insert that may be combined with an annular skirted cap body to create the cap apparatus required by a customer. Cap insert parts having different features such as ports or vents or filters are interchangeable, and fit into the annular skirted cap body. The dimensions of the annular skirted cap body dictate the coupling between the cap and the container. The cap insert dictates the nature of the connectors and features found in the cap apparatus. Because of this method of assembly, there are numerous embodiments of cap apparatus disclosed herein. Only a few of these embodiments are shown in FIG. 2A-D.

Figure 3:
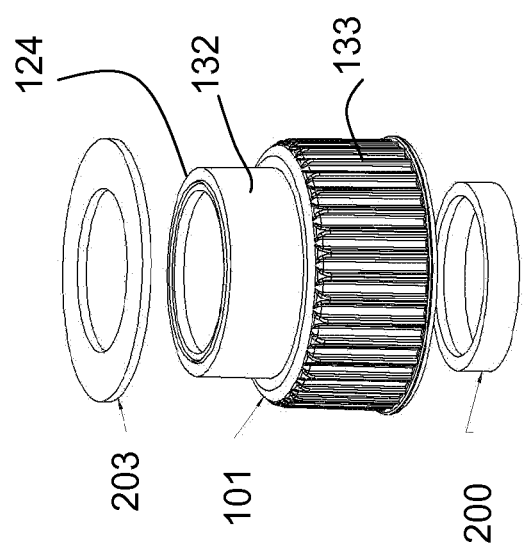
FIG. 3 is an exploded view of a partially assembled embodiment of the cap apparatus.

FIG. 3 is an exploded view of a partially assembled embodiment of the cap apparatus. Shown in FIG. 3 is an annular thrust bearing 203, an embodiment of the annular skirted cap body 101 and an flanged bearing 200. The embodiment shown in FIG. 3 is a double-skirted annular cap body, having two skirts, 132 and 133. The flanged bearing 200 is inserted into the skirted cap body 101 from below, and the thrust bearing 203 is coupled to the annular top wall 124 of the skirted cap body 122. Also illustrated in FIG. 3 is that the outer surface of the annular skirted cap body may be texturized to improve manipulation of the cap in relation to the container. The flanged bearing 200 is pressed into the annular skirted cap body 101. The flanged bearing 200 and the thrust bearing 203 may be coupled to the annular skirted cap body 101 by any means known in the art including press-fitting, welding, heat-sealing or other methods. The thrust bearing, for example, may be ultrasonically welded to the face of the cap. The flanged bearing 200 and thrust bearing 203 are annular to allow the cap insert to pass through the center opening of the skirted cap body 101.

Figure 4:
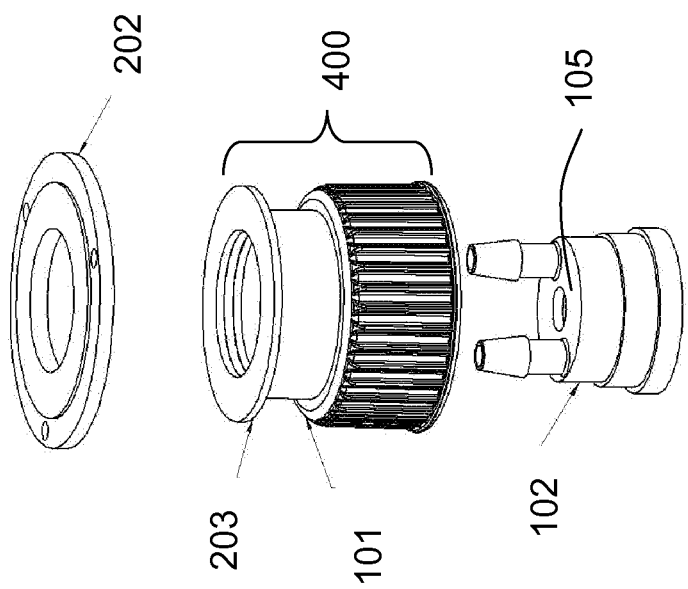
FIG. 4 is an additional exploded view of a partially assembled embodiment of the cap apparatus.

FIG. 4 is an additional exploded view of a partially assembled embodiment of the cap apparatus. FIG. 4 shows the annular skirted cap body 122 with the thrust bearing 203 attached to its annular top wall 124 (not shown in FIG. 4). The cap insert 102 is shown. The cap insert has a top face 105. Also shown in FIG. 4 is the anti-rotation mounting plate 202. Once the cap insert 102 is assembled through the annular skirted cap body and bearing assembly 400, the anti-rotation mounting plate 202 is pressed onto the cap insert 102. In embodiments, the anti-rotation mounting plate 202 is attached onto the cap insert 102 by, for example, a radial press fit such that the cap insert 102 and anti-rotation mounting plate 202 are solidly joined as one. In embodiments, iIt is pressed to an axial distance to allow clearance for the cap and bearing assembly to freely rotate.

Figure 5:
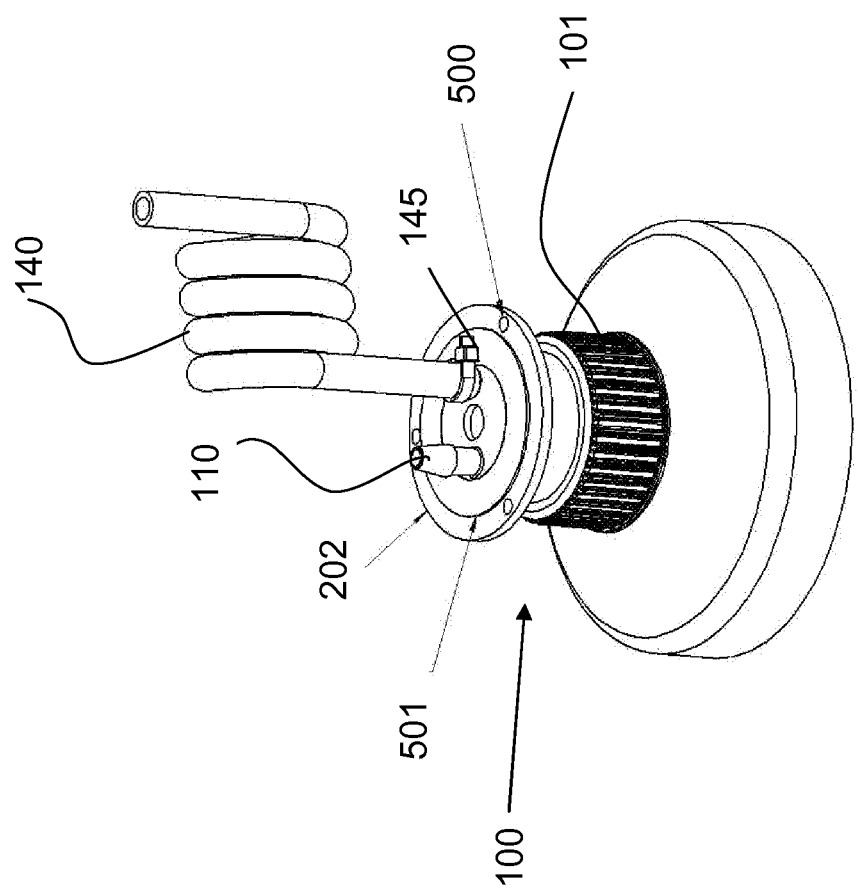
FIG. 5 is a perspective view of an embodiment of an assembled cap apparatus.

FIG. 5 is a perspective view of an embodiment of an assembled cap apparatus 100. FIG. 5 shows the annular skirted cap body and bearing assembly 400, with the cap insert threaded through the skirted cap body 101. Ports 110 extend from the top face of the assembly. Tubing 140 is shown attached to one port 110. Tubing may be attached to the port using a clamp 145. The anti-rotation mounting plate 202 also shows a pilot diameter for mounting 501. This additional diameter on the anti-rotation mounting plate 202 lends additional diameter that may be used to couple the anti-rotation mounting plate 202 to another apparatus (not shown). The anti-rotation mounting plate 202 may have mounting holes 500. In embodiments, these mounting holes may be threaded. These mounting holes may be used to couple the anti-rotation mounting plate 202 to another apparatus (not shown).

Figure 6:
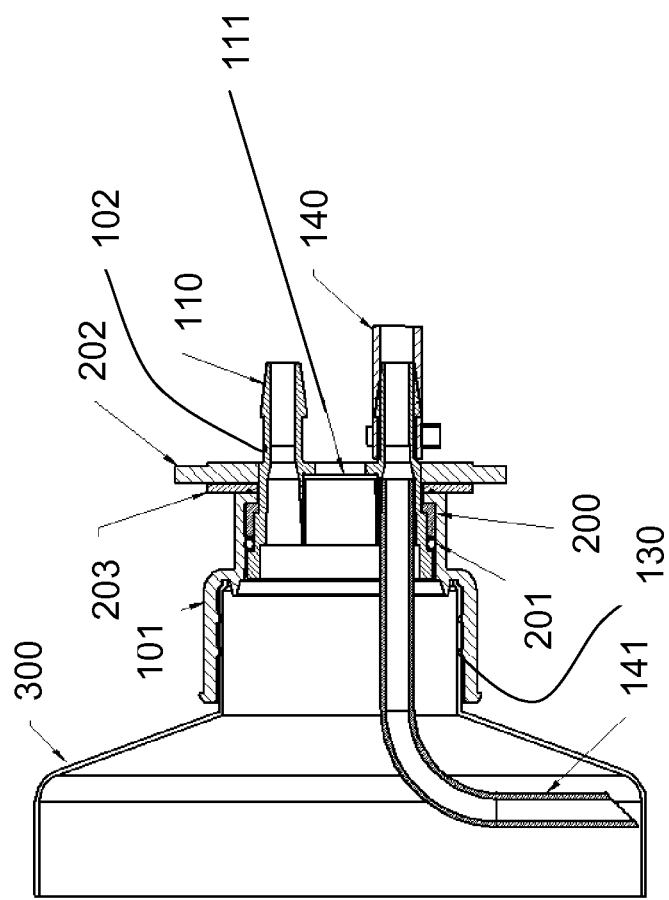
FIG. 6 cross-sectional view of an embodiment of a cap apparatus, attached to a container.

FIG. 6 is a cross-sectional view of an embodiment of a cap apparatus 101, attached to a roller bottle 300. FIG. 6 shows the cap apparatus for the roller bottle aseptic closed system. To maintain the closed environment, the cap and tubing set must be able to tolerate rotation of the roller bottle vessel while remaining stationary itself. If the tubing rotated with the bottle, the tubing set would tangle and eventually detach itself. A flanged bearing 200 is pressed into the cap 101. It can be secured by adhesive, weld, or press fit into the housing of the cap. It is made of a suitable bearing material. An annular thrust bearing 203 is secured to the outer surface of the top side of the cap. It too can be secured by adhesive or weld. The annular thrust bearing 203 has a top surface. An o-ring 201 is inserted into annular skirted cap body 101 right behind the flanged bearing 200. The annular skirted cap body has a connector to connect to the container. Shown in FIG. 6 are threads 130 to connect to a threaded neck of the container 300. Other connectors may also be used, including a snap-fit connector, for example.

The cap insert 102 is slipped into the annular skirted cap body 101, (from left to right), making contact with the flanged bearing 200 and then the o-ring 201, so that the at least one port extends from the top of the cap apparatus. The o-ring 201 will prevent any wear debris from the bearings from entering into the container or vessel 300. The anti-rotation mounting plate 202 is then pressed onto the cap insert 102. Relative rotation occurs at the inside diameter of the flanged bearing 200 and the outer face of the thrust bearing 203. Dip tubes 141 and tubing set accessories 140 are then added to the cap apparatus. The entire cap and tubing accessory is then screwed into the roller bottle to complete the assembly. Relative rotation occurs at the inside diameter of the flanged bearing 200 and the outer face of the thrust bearing 203. Tubing 140 is shown coupled to a port 110. A dip tube 141 is also shown inserted into the interior of the vessel 300. The dip tube allows liquid to be removed from the container or vessel without removing the cap apparatus 100. It is important to note that if the cap has a right hand thread, the bottle is limited to only counterclockwise rotation as viewed from the cap end of the bottle. Otherwise, the cap would unscrew itself.

Figure 7:
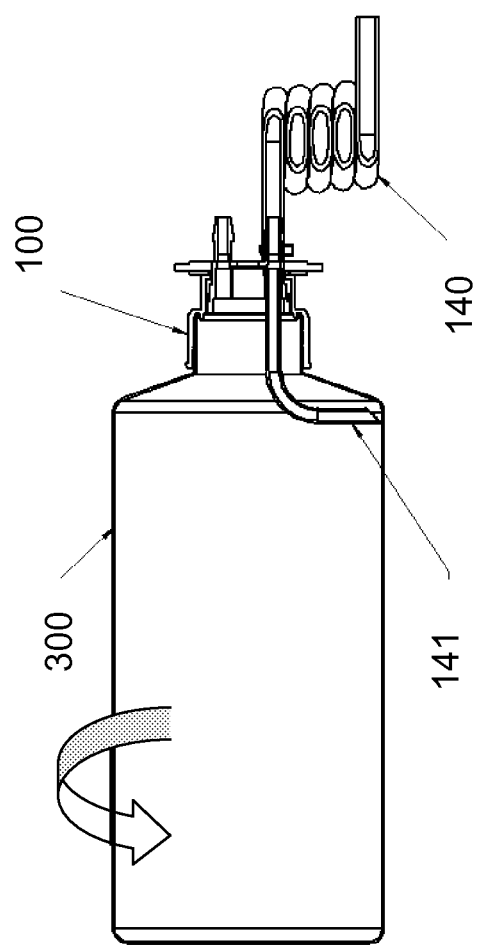
FIG. 7 is an illustration of an embodiment of a roller bottle with an embodiment of a cap apparatus of the present invention.

FIG. 7 is an illustration of an embodiment of a roller bottle 300 with an embodiment of a cap apparatus 100 of the present invention. As the roller bottle rotates (clockwise, as shown by the arrow), the ports coupled to tubing 140 do not rotate. And, the dip tube 141, extending into the interior of the roller bottle 300, also does not rotate.

4 is a top-down view of an embodiment of a cap apparatus on a container. FIG. 4 illustrates the container 300. The annular skirted cap body 120 is attached to the neck of the vessel 300 by threads 130. The anti-rotation mounting plate 202 is attached, on it's underside, to the thrust bearing 203. The cap insert 102 is attached to the anti-rotation mounting plate 202. The cap insert as shown has two ports 110 and one vent 111.

Figure 8:
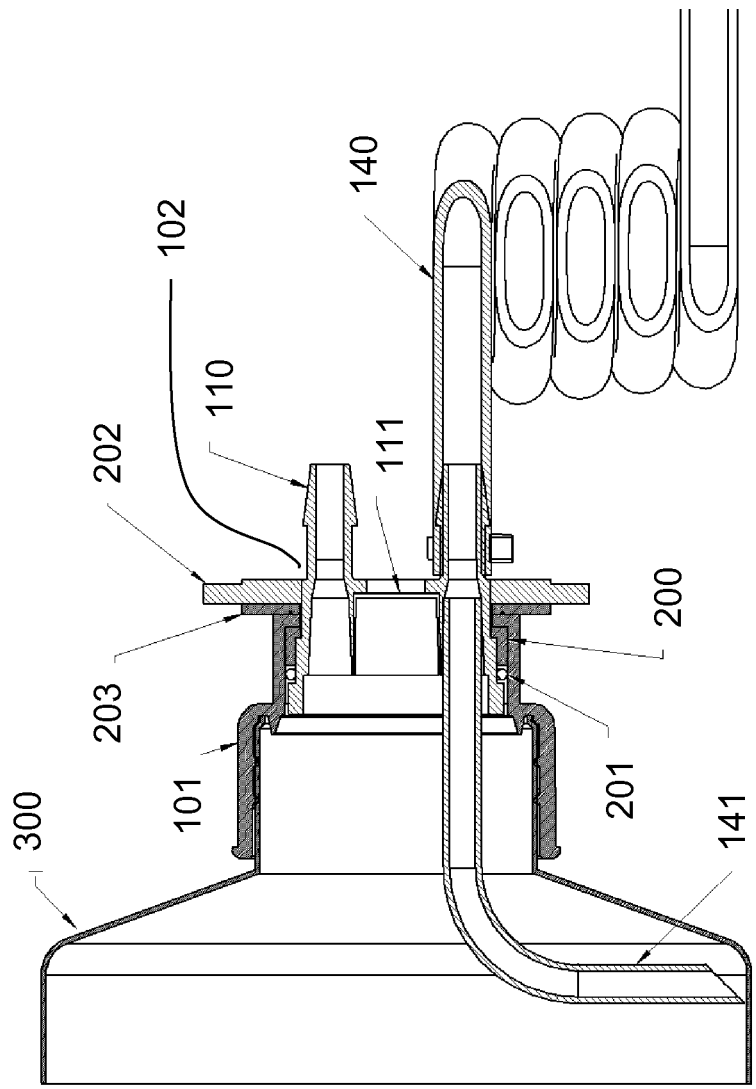
FIG. 8 is a cross-sectional view of an embodiment of the cap apparatus on a container, showing in dark areas the regions of the cap apparatus that rotate with the container.

FIG. 8 is an additional cross-sectional view of an embodiment of the cap apparatus on a container, showing in dark areas the regions of the cap apparatus that rotate with the container. FIG. 8 illustrates an embodiment of a cap apparatus 101, attached to a roller bottle 300. FIG. 8 shows the cap apparatus for the roller bottle aseptic closed system. To maintain the closed environment, the cap and tubing set must be able to tolerate rotation of the roller bottle vessel while remaining stationary itself. If the tubing rotated with the bottle, the tubing set would tangle and eventually detach itself. A flanged bearing 200 is pressed into the cap 101. It can be secured by adhesive, weld, or press fit into the housing of the cap. It is made of a suitable bearing material. An annular thrust bearing 203 is secured to the outer surface of the top side of the cap. It too can be secured by adhesive or weld, or by any suitable method. The annular thrust bearing 203 has a top surface. An o-ring 201 is inserted into annular skirted cap body 101 behind the flanged bearing 200.

The cap insert 102 is slipped into the annular skirted cap body 101, (from left to right), making contact with the flanged bearing 200 and then the o-ring 201. The o-ring 201 will prevent any wear debris from the bearings from entering into the container or vessel 300. The anti-rotation mounting plate 202 is then pressed onto the cap insert 102. Relative rotation occurs at the inside diameter of the flanged bearing 200 and the outer face of the thrust bearing 203. Dip tubes 141 and tubing set accessories 140 are then added to the cap apparatus. The entire cap and tubing accessory is then screwed into the roller bottle to complete the assembly. Relative rotation occurs at the inside diameter of the flanged bearing 200 and the outer face of the thrust bearing 203. Tubing 140 is shown coupled to a port 110. A dip tube 141 is also shown inserted into the interior of the vessel 300. The dip tube allows liquid to be removed from the container or vessel without removing the cap apparatus 100. It is important to note that if the cap has a right hand thread, the bottle is limited to only counterclockwise rotation as viewed from the cap end of the bottle. Otherwise, the cap would unscrew itself.

The dark shaded region in FIG. 8 illustrates parts of the cap apparatus which rotate along with the container or vessel. The roller bottle 300, annular skirted cap body 101, flanged bearing 200 and thrust bearing 203 all rotate as one unit, upon the rotation of the container or bottle. Typical rotation speed in under 5 rpm. The cap insert 102, dip tubing 141, anti-rotation mounting plate 202 and tubing 140 are stationary. They are held stationary by securing a portion of the cap insert 102, tubing 140 or anti-rotation mounting plate 202 to a frame or equipment or some other available bulkhead that is immobile (unmovable). Relative rotational motion occurs at the inside diameter of the flanged bearing and an outside diameter of the cap insert. Relative motion also occurs between the face of the thrust bearing and the face of the anti-rotation mounting plate. For optimal operation, proper perpendicularity and axial alignment must be maintained when attaching the anti-rotation mounting plate or pre-mature wear of the bearings may occur. Flexible couplings mounted between the anti-rotation mounting plate and the bulkhead could help account for any gross misalignment.

Figure 9:
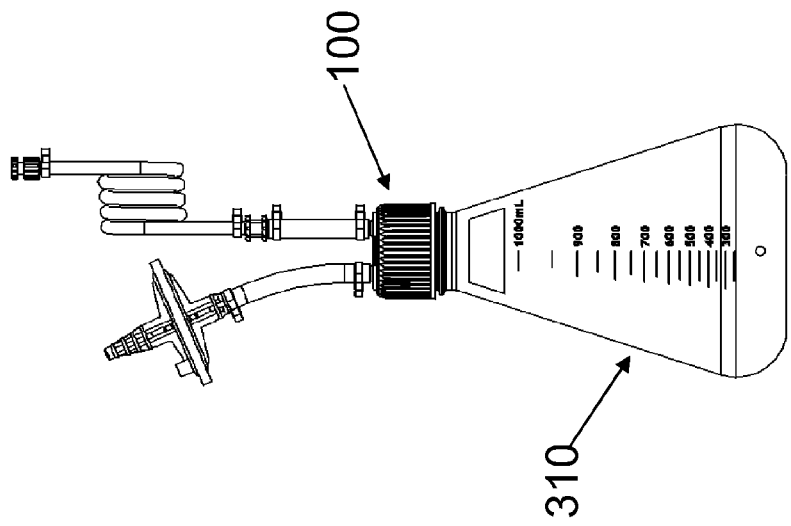
FIG. 9 is an additional embodiment of the cap apparatus coupled to a flask.

FIG. 9 is an illustration of an additional embodiment of a use of the cap apparatus 100 disclosed herein, used in association with a flask 310. Flasks are often used in applications that require shaking or motion. While this motion may not be rolling motion, the motion may cause the same concerns about keeping tubing un-kinked. Thus, embodiments of Container Cap with Kink-Resistant Connector are disclosed. One skilled in the art will appreciate that the apparatus and methods described herein can be practiced with embodiments other than those disclosed. The disclosed embodiments are presented for purposes of illustration and not limitation.

What is claimed is:
1. A cap comprising;
an annular anti-rotation mounting plate; and
a cap apparatus assembled from two parts;
(1) a cap body and bearing assembly comprising (a) an annular skirted cap body having a side wall and a central opening defining an inner surface of the cap body, an annular top wall having an annular outer surface and an annular undersurface, (b) a flanged bearing secured to the undersurface of the annular top wall, and (c) an annular thrust bearing secured to the annular outer surface of the annular top wall, the thrust bearing having an outer surface; and, (2) a cap insert having at least one port;
wherein the inner surface of the annular skirted cap body has a connector to connect the cap body to a container;
wherein the cap insert is seated inside the skirted cap body so that the annular skirted cap body and the cap insert are coupled through the flanged bearing, and the at least one port extends through the central opening of the annular skirted cap body;
and wherein the cap insert is attached to the annular anti-rotation mounting plate,
wherein the cap is configured such that, when secured relative to a container, the annular skirted cap body, flanged bearing and thrust bearing rotate as the container rotates, while the cap insert and anti-rotation mounting plate remain stationary as the container rotates.

2. The cap of claim 1 further comprising an O-ring seated against the flanged bearing.

3. The cap of claim 2 wherein the O-ring is seated between the flanged bearing and the cap insert.

4. The cap of claim 1 wherein the cap insert has at least two ports.

5. The cap of claim 1 wherein the cap insert comprises a vent.

6. The cap of claim 1 wherein the cap insert comprises a filter.

7. The cap of claim 5 wherein the vent comprises an adjustable vent opening.

8. The cap of claim 1 further comprising a container structured and arranged to engage with the cap apparatus.

9. The cap of claim 8 wherein the container comprises threading.

10. The cap of claim 9 wherein the cap comprises threading structured and arranged to engage with the threading of the container, to secure the cap against a container.

11. The cap of claim 10 wherein the cap is removably secured to the container.

12. The cap of claim 10 wherein the cap is permanently secured to the container.

13. The cap of claim 1 wherein the annular skirted cap body is double skirted having a first skirt and second skirts, wherein the first skirt is adjacent the annular top wall, wherein the first skirt is between the annular top wall and the second skirt, and wherein the first has an outer diameter smaller than the second skirt.

14. The cap apparatus of claim 1 wherein the annular anti-rotation mounting plate comprises mounting holes.

15. The cap of claim 14 wherein the mounting holes are threaded.

16. The cap of claim 1, wherein relative rotation is configured to occur at an inside diameter of the flanged bearing and an outer face of the thrust bearing.

17. A cap comprising;
an annular anti-rotation mounting plate; and
a cap apparatus assembled from two parts;
(1) a cap body and bearing assembly comprising (a) an annular skirted cap body having a side wall and a central opening defining an inner surface of the cap body, an annular top wall having an annular outer surface and an annular undersurface, (b) a flanged bearing secured to the undersurface of the annular top wall, and (c) an annular thrust bearing secured to the annular outer surface of the annular top wall, the thrust bearing having an outer surface; and, (2) a cap insert having at least one port;
wherein the inner surface of the annular skirted cap body has a connector to connect the cap body to a container;
wherein the cap insert is seated inside the skirted cap body so that the annular skirted cap body and the cap insert are coupled through the flanged bearing, and the at least one port extends through the central opening of the annular skirted cap body;
and wherein the cap insert is attached to the annular anti-rotation mounting plate,
wherein the cap further comprises an O-ring seated against the flanged bearing.

18. The cap of claim 17 wherein the O-ring is seated between the flanged bearing and the cap insert.

19. A cap comprising;
an annular anti-rotation mounting plate comprising threaded mounting holes; and
a cap apparatus assembled from two parts;
(1) a cap body and bearing assembly comprising (a) an annular skirted cap body having a side wall and a central opening defining an inner surface of the cap body, an annular top wall having an annular outer surface and an annular undersurface, (b) a flanged bearing secured to the undersurface of the annular top wall, and (c) an annular thrust bearing secured to the annular outer surface of the annular top wall, the thrust bearing having an outer surface; and,
(2) a cap insert having at least one port;
wherein the inner surface of the annular skirted cap body has a connector to connect the cap body to a container;
wherein the cap insert is seated inside the skirted cap body so that the annular skirted cap body and the cap insert are coupled through the flanged bearing to allow the cap insert to rotate within the central opening of the skirted cap body, and the at least one port extends through the central opening of the annular skirted cap body;
and wherein the cap insert is attached to the annular anti-rotation mounting plate.

\* \* \* \* \*